US00PP37255P2

(12) United States Plant Patent
Moon

(10) Patent No.: US PP37,255 P2
(45) Date of Patent: Feb. 10, 2026

(54) ***CHIONANTHUS* TREE NAMED 'CRMTF'**

(50) Latin Name: *Chionanthus retusus*
Varietal Denomination: CRMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 19/083,810

(22) Filed: Mar. 19, 2025

(51) Int. Cl.
*A01H 5/02* (2018.01)
*A01H 6/00* (2018.01)

(52) U.S. Cl.
USPC ..... Plt./216

(58) Field of Classification Search
USPC ..... Plt./216, 226
CPC ..... A01H 5/02; A01H 5/00; A01H 6/00
See application file for complete search history.

(56) References Cited

PUBLICATIONS

Sutton, *Chionantus retusus*, Trees and Shrub online 2022, retrieved on May 22, 2025 at https://www.treesandshrubsonline.org/articles/chionanthus/chionanthus-retusus/, 14 pp. (Year: 2022).*

* cited by examiner

*Primary Examiner* — June Hwu

(57) ABSTRACT

A new and distinct cultivar of *Chionanthus retusus* tree named 'CRMTF' is disclosed, characterized by a fast growth rate, prolific white flowers and dark green foliage. The new variety is easily propagated by softwood cuttings. The new variety is a *Chionanthus* tree, typically used for landscapes and gardens.

6 Drawing Sheets

Latin name of the genus and species: *Chionanthus retusus*.

Variety denomination: 'CRMTF'.

BACKGROUND OF THE INVENTION

The inventor discovered the new cultivar in the Summer of 2019 growing as a seedling in a production field in at a tree farm in Washington, Georgia, among a group of cross-pollinated *Chionanthus retusus*. The cross-pollination resulting in the new variety is assumed to have occurred during 2017. Evaluation of this tree has continued on a tree farm located in Washington, Georgia, Wilkes County.

Asexual reproduction by grafting of the new cultivar 'CRMTF' was first performed during the Summer of 2020 at a commercial nursery in Washington, Georgia. Asexual propagation has resulted in progeny that have proven the characteristics of the new variety to be genetically stable. This propagation process involved taking softwood cuttings in June, placing them under mist for approximately six weeks. The cuttings are then moved into 3"×6" tree band pots and placed outside on container growing pads. Furthermore, these observations have confirmed that the new variety represents a new and improved variety of Chinese Fringe tree as particularly evidenced by the prolific white flowers These genetic traits can be consistently reproduced by asexual propagation.

SUMMARY OF THE INVENTION

The cultivar 'CRMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CRMTF' grown in Washington, Georgia. These characteristics in combination distinguish 'CRMTF' as a new and distinct *Chionanthus retusus* cultivar:

1. Prolific white flowers.
2. Ease of softwood propagation.
3. Dark green foliage.
4. Fast growth rate. A 3-gallon pot is saleable with a 2 inch caliper in 2 full Summers.

PARENT COMPARISON

The parent varieties cannot be specifically identified.

COMMERCIAL COMPARISON

Trees of the new cultivar 'CRMTF' are similar to trees of the commercial variety, *Chionanthus virginicus* 'CVJMW', U.S. Plant Pat. No. 36,524, in most horticultural characteristics. However, plants of the new cultivar 'CRMTF' differ in the following:

1. The new variety grows faster than this comparator, filling a 3-gallon pot more fully in 2 summer seasons.
2. The new variety has pure white petals; this comparator has green-white petals.
3. The new variety has a denser canopy than this comparator.
4. The new variety produces berries; this comparator produces no berries.

Plants of the new cultivar 'CRMTF' are similar to trees of the species, *Chionanthus retusus* found in the nursery trade in most horticultural characteristics. However, plants of the new cultivar 'CRMTF' differ in the following:

1. The new variety roots more easily from softwood cuttings than the species.

2. The new variety has narrower, and more upright growth than the species.
3. The new variety is more floriferous than the species.

BRIEF DESCRIPTION OF THE PHOTOGRAPHS

The accompanying photograph in FIG. 1 illustrates a tree of the new variety at about 4 years of age planted in a field. The photograph was taken during winter while the tree has no foliage, allowing the branch structure to be clearly seen.

Figure 1:
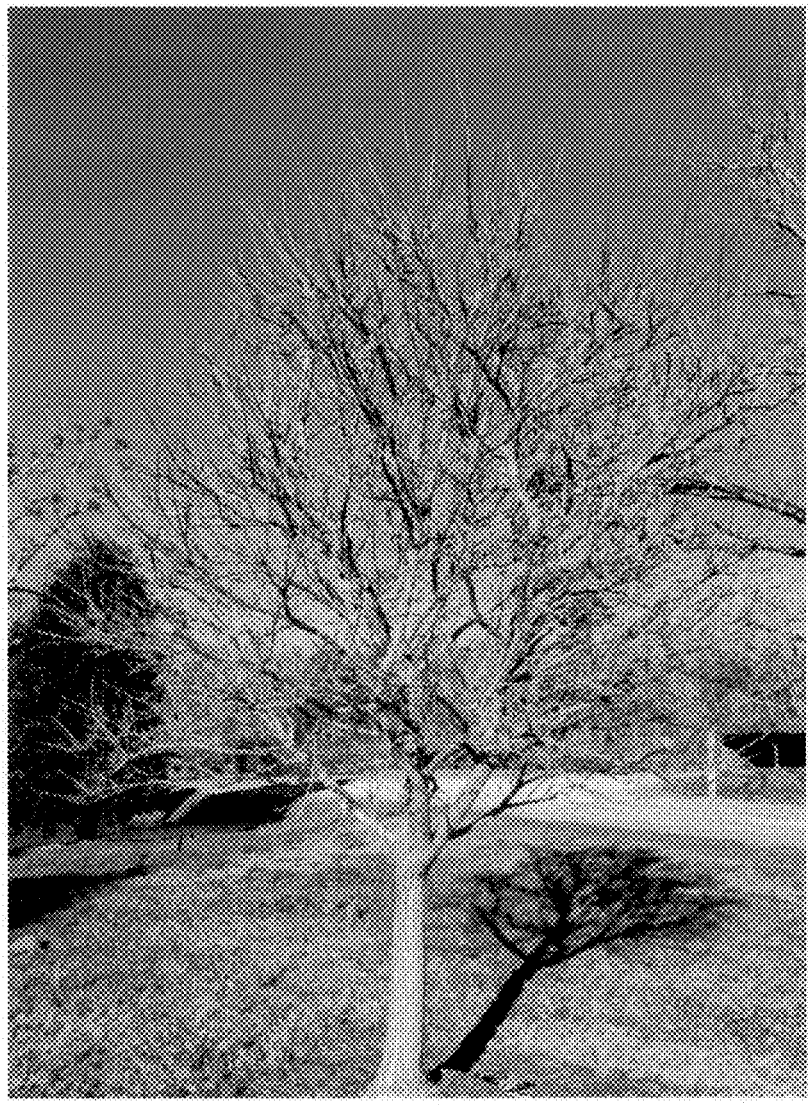
Figure 2:
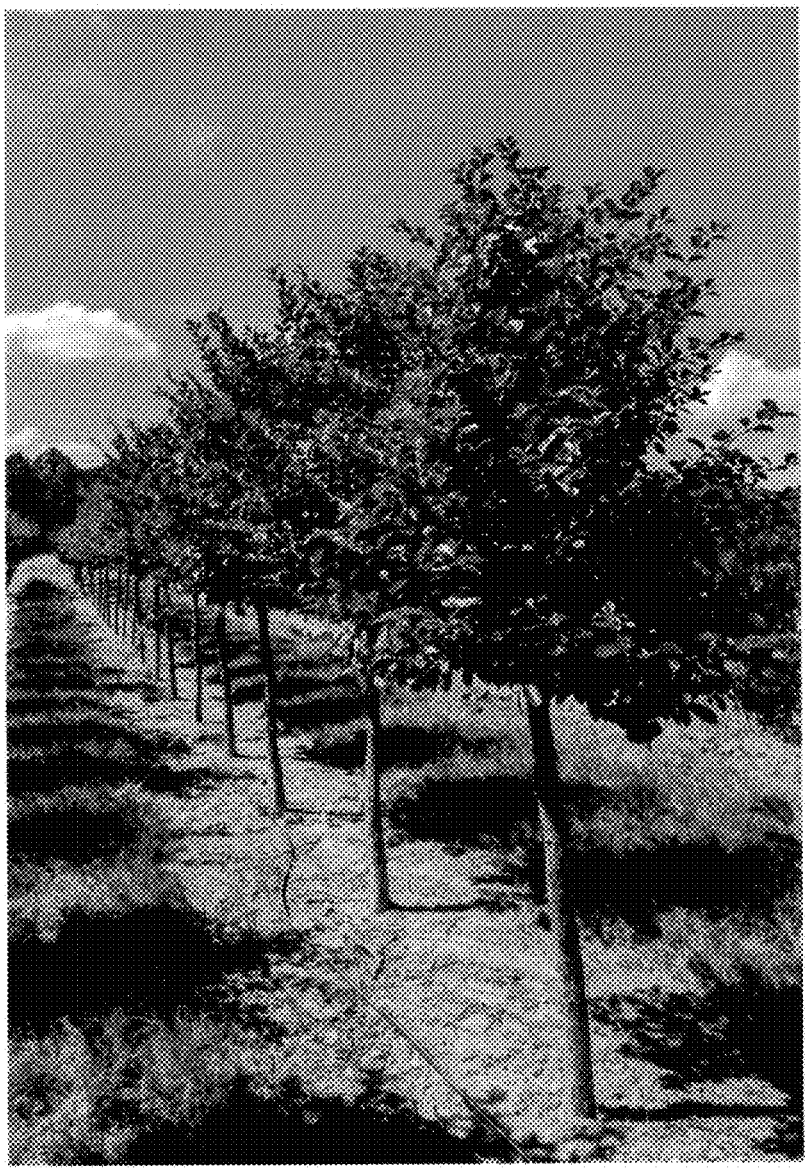
FIG. 2 is a photograph of several trees of the new cultivar of about 4-years old during late Summer in Washington, GA.
Figure 3:
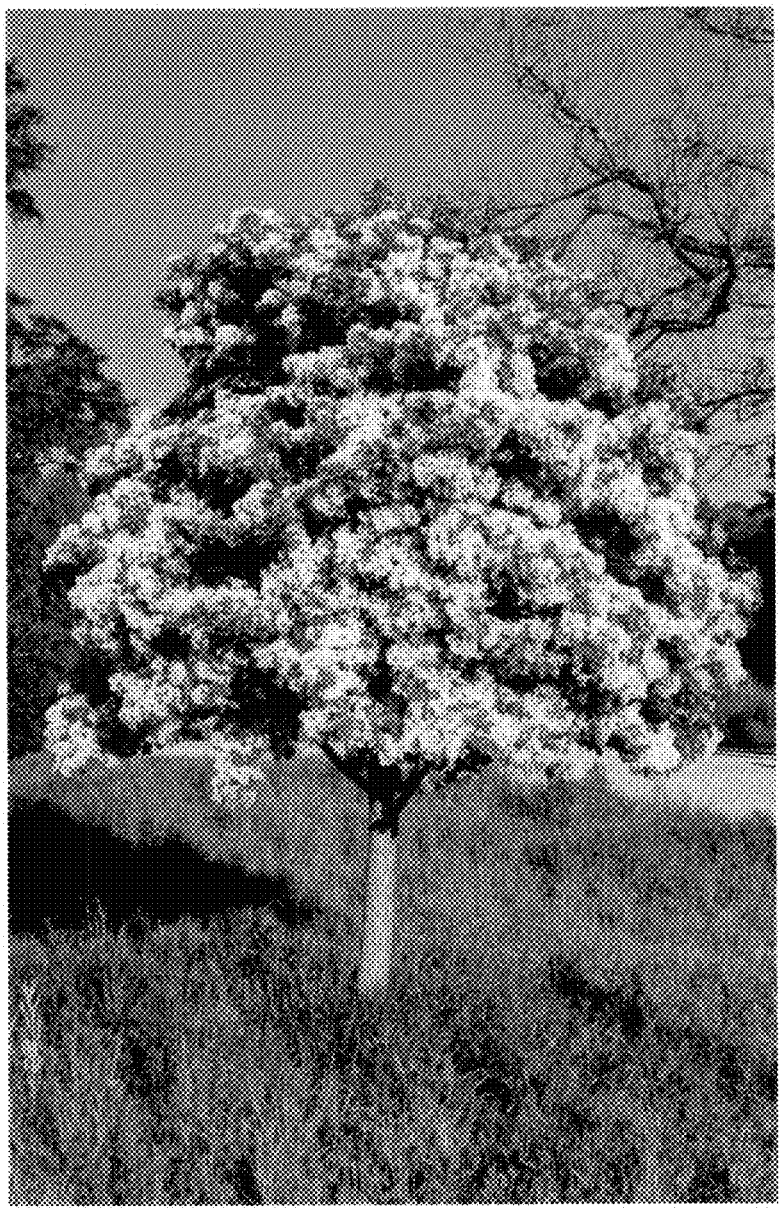
FIG. 3 is a flowering tree of about 5 years old during Spring.
Figure 4:
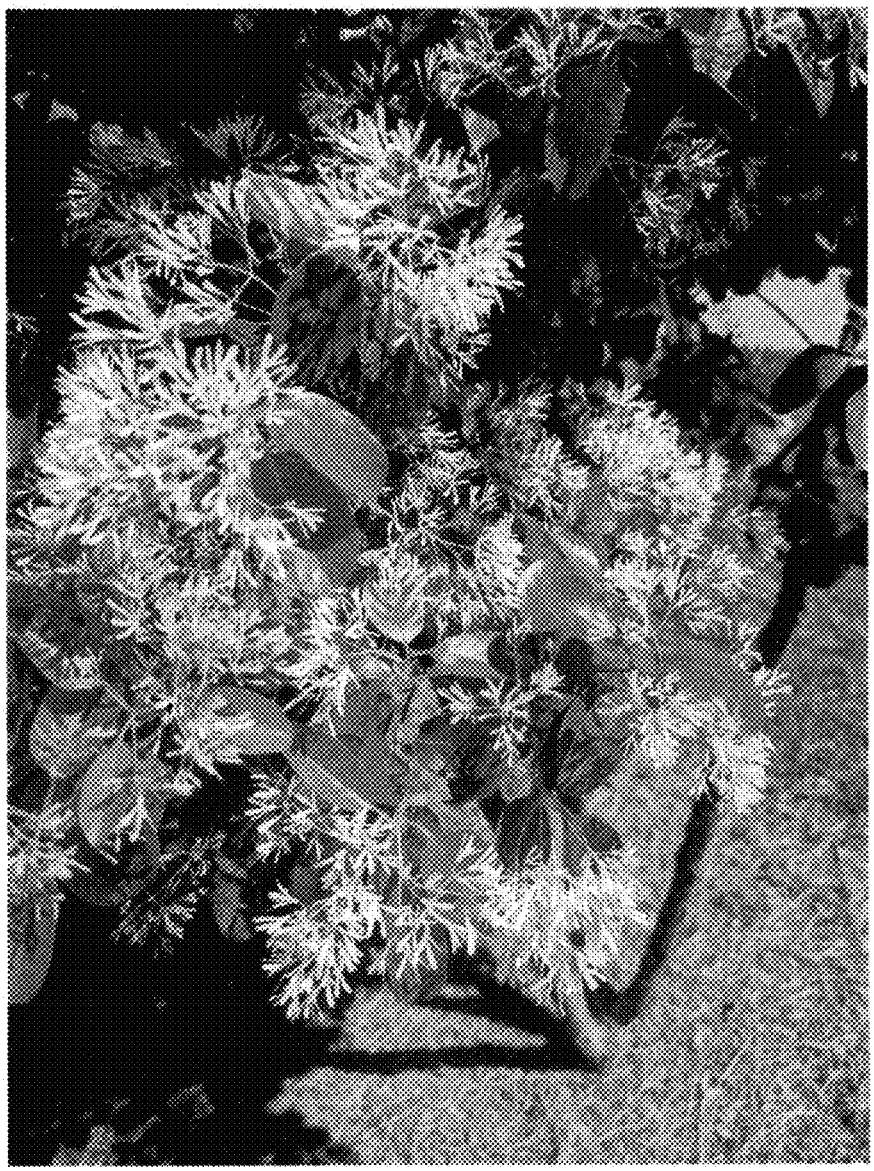
FIG. 4 is a close-up view of inflorescences and young foliage.
Figure 5:
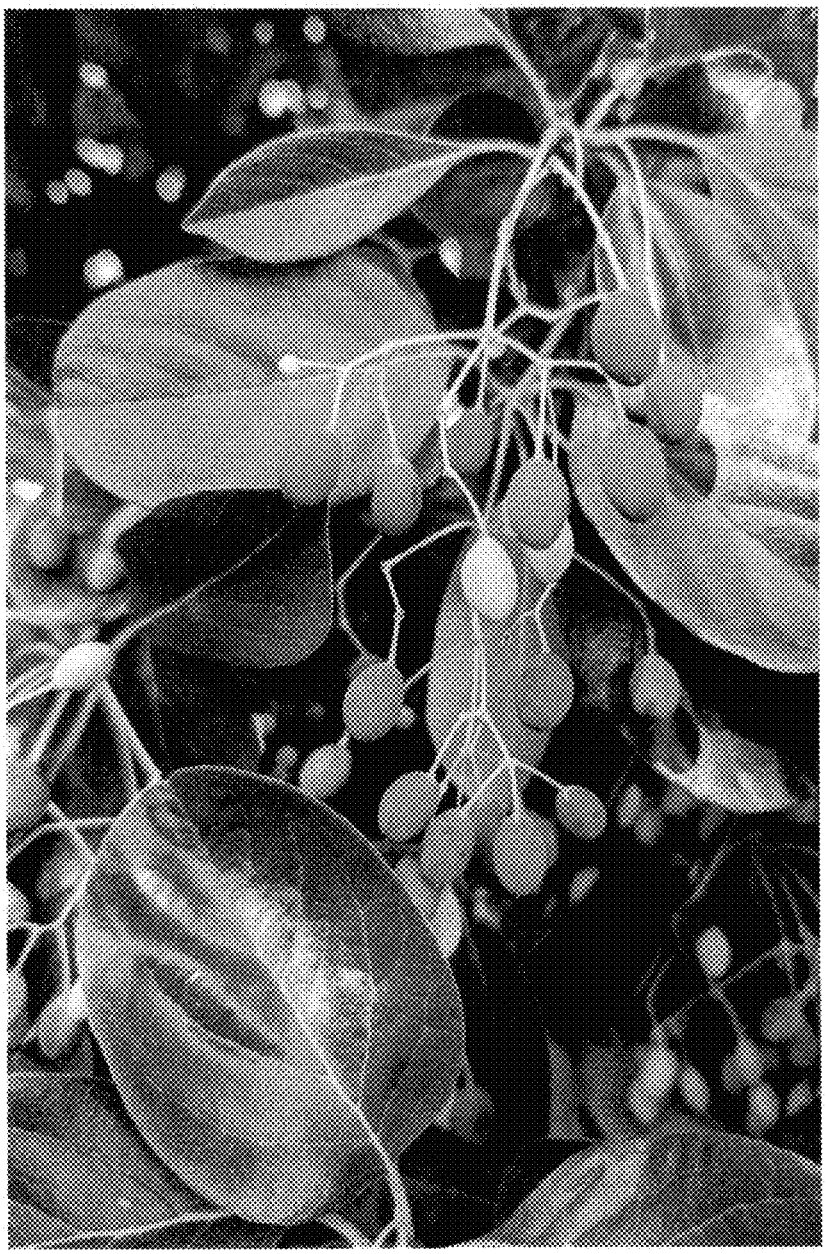
FIG. 5 illustrates mature and immature fruits.
Figure 6:
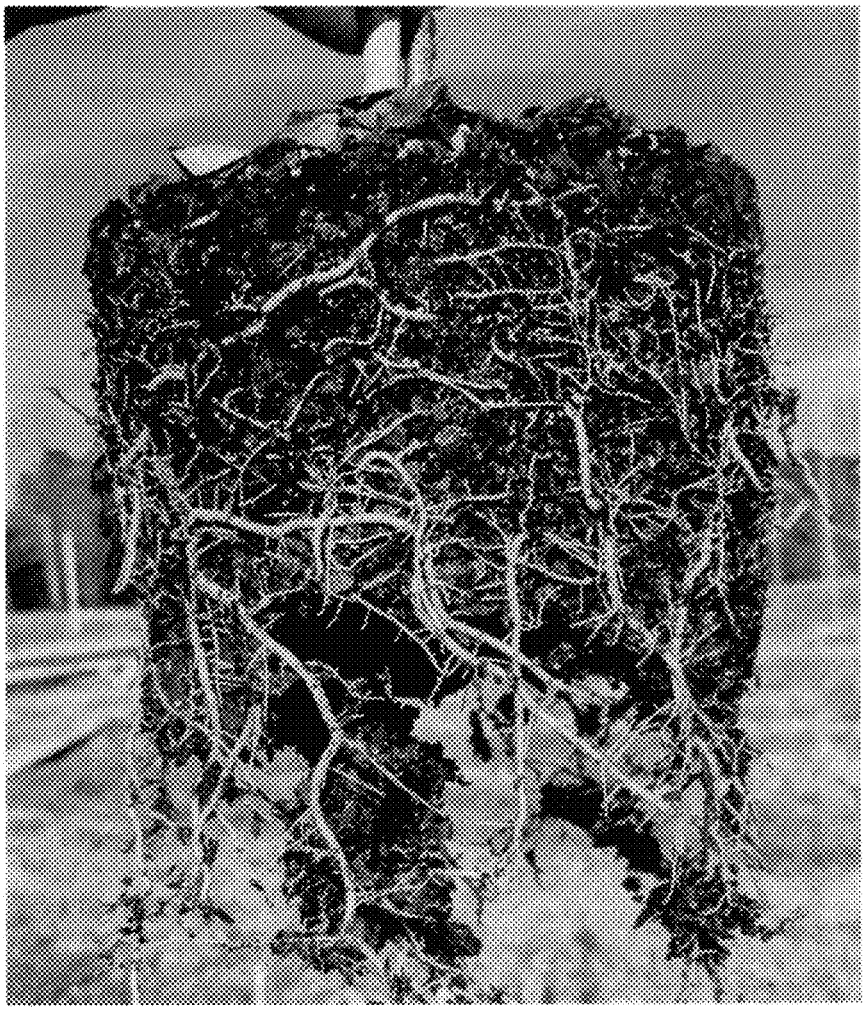
FIG. 6 shows the roots produced in a 3-gallon pot at approximately 1.5 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CRMTF' plants grown outdoors and in a nursery in Washington, Georgia. Plants are approximately 1.5 years old, in a 3-gallon nursery container. Temperatures ranged from 5° C. to 10° C. at night to 18° C. to 27° C. during the day. Measurements and numerical values represent averages of typical plant types.

Botanical classification: *Chionanthus retusus* 'CRMTF'.

PROPAGATION

Softwood cuttings.

Root description: Dense, fibrous. Moderately dense. Brown 200B.

TREE

Plant type: Deciduous flowering tree.

Height of tree described: 100 cm.

Spread of tree described: 35 cm.

Tree shape: Round.

Growth rate: A 3-gallon pot is saleable with a 2 inch caliper trunk in 2 full Summers.

Trunk color: Near RHS Grey-Brown N199A streaked Greyed-Orange 166A, 166D and 165A.

Trunk diameter: As a single trunk main trunk is 7.4 cm at 6 cm from ground level.

Trunk texture: Scaly. Scales colored Greyed-Green 198C and Grey-Brown 199C.

Branching characteristics:

Quantity of lateral branches: 2 main branches from base (pinched), each of these produces 3 to 4 main lateral branches Diameter of lateral branches: Approximately 5 o 6 mm.

Length of lateral branches: 20 to 30 cm.

Texture of lateral branches: Glabrous.

Color of lateral branches: Young: Near RHS Green 143A. Mature: Near Greyed-Green 198A.

Aspect and angle: Acute.

Strength of lateral branches: Strong and somewhat flexible.

Branches occur how far apart: Approximately 5 to 10 on cm on a 1-year-old sapling.

Other branch or trunk characteristics:

*Lenticels present.*—Yes, moderately dense.

*Lenticel width.*—Approximately 1 to 2 mm long and 1 mm wide.

*Lenticel color.*—About RHS Greyed-Orange 166C.

FOLIAGE

Leaf:

*Type/arrangement.*—Opposite or sub-opposite.

*Average length.*—Approximately 7 to 9 cm.

*Average width.*—Approximately 4 to 5 cm.

*Shape of blade.*—Ovate.

*Apex.*—Acute. Oldest, lowest foliage blunt and shallowly notched.

*Base.*—Broad attenuate, oldest, lowest foliage truncate.

*Attachment.*—Petiolate.

*Margin.*—Entire. Oldest, lowest foliage develops very shallow crenations.

*Texture of top surface.*—Glabrous.

*Texture of bottom surface.*—Glabrous.

*Appearance of top surface.*—Very glossy.

*Appearance of bottom surface.*—Matte.

*Leaf internode length.*—Average 3 cm.

*Color.*—Young foliage upper side: Near RHS Yellow-Green N144A. Young foliage under side: Near RHS Green 143C. Mature foliage upper side: Near RHS Green 136A. Mature foliage under side: Near RHS Green 138B. Fall foliage upper side: Near RHS Yellow 5A. Fall foliage under side: Near RHS Yellow 9B.

*Venation.*—Type: Pinnate. Venation color: Upper Surface: Green 143B. Lower Surface: Green 143D.

Petiole:

*Length.*—1 cm.

*Diameter.*—3 mm.

*Color.*—RHS Green 143B.

*Texture.*—Glabrous.

FLOWER

Inflorescence and flower type and habit: Semi-pendant panicles produced terminally and from leaf axils.

Inflorescence shape: Irregular globular.

Inflorescence diameter: 8 to 12 cm.

Inflorescence depth: 5 to 8 cm

Flower shape: 4 (occasionally 3 or 5) strap-like petals forming an irregular, open star.

Individual flower diameter: 2.5 cm.

Individual flower depth: 2 to 2.8 cm

Quantity of flowers per inflorescence: 10 to 30.

Persistence: Self-Cleaning.

Fragrance: Moderate to strong.

Flower buds:

*Shape.*—Orbicular.

*Length.*—About 8 mm.

*Diameter.*—About 8 mm.

*Color.*—RHS Green-White 157C.

Petals:

*Quantity per flower.*—4.

*Shape*.—Strap-shaped.
*Margin*.—Entire.
*Texture*.—Smooth.
*Length*.—About 1.1 cm.
*Width*.—About 5 mm.
*Apex*.—Rounded.
*Base*.—Attenuate.
*Color*.—Upper surface: RHS White 155C. Lower surface: RHS White 155C.

Sepals:
*Quantity per flower*.—4, fused.
*Texture*.—Pubescent.
*Arrangement*.—Opposite.
*Shape*.—Ovate.
*Length*.—3 mm.
*Width*.—2 mm.
*Apex*.—Acute.
*Base*.—Fused onto calyx.
*Margin*.—Entire.
*Color*.—Inner surface: RHS Green 143C. Outer surface: RHS Green 143A.

Peduncle:
*Primary*.—
*Length*.—About 5 to 6 cm.
*Diameter*.—About 3 mm.
*Texture*.—Glabrous.
*Strength*.—Moderate, flexible.
*Color*.—RHS Yellow-Green 151C.
*Secondary*.—
*Length*.—About 3 cm.
*Diameter*.—About 3 mm.
*Texture*.—Glabrous.
*Strength*.—Moderate, flexible.
*Color*.—RHS Yellow-Green 150D.

REPRODUCTIVE ORGANS

Androecium: Not observed.

Pistil:
*Number*.—1 pistil per flower.
*Length*.—Approximately 2 mm.
*Color*.—RHS White 155D.
*Style*.—Length: 1 mm. Color: RHS White 155D.
*Stigma*.—Shape: Rounded. Color: RHS White 155A. Ovary: Length: 1 mm. Width: 1 mm. Color: RHS White 155D.

OTHER CHARACTERISTICS

Fruit:
*Type*.—Drupe.
*Size*.—7 to 15 mm long, 5 to 8 mm wide.
*Shape*.—Ovate.
*Color*.—Immature: Yellow-Green 144D. Mature: Blue 99A with strong overall glaucous layer violet-Blue 97D.
*Seeds*.—1. About 1.5 mm long, 1 mm wide. Colored Brown 200B.

Disease/pest resistance: Neither resistance nor susceptibility to normal diseases and pests of *Chionanthus* has been observed.

Drought tolerance: No tolerance for drought observed. *Chionanthus retusus* can be slightly drought tolerant once established.

Temperature tolerance: USDA Zones 5 through 9.

What is claimed is:

1. A new and distinct cultivar of *Chionanthus retusus* tree named 'CRMTF' as herein illustrated and described.

* * * * *